US010309881B2

(12) United States Patent
Glaeser et al.

(10) Patent No.: US 10,309,881 B2
(45) Date of Patent: Jun. 4, 2019

(54) METHODS AND APPARATUS FOR PREPARING AQUEOUS SPECIMENS FOR ELECTRON MICROSCOPY USING VOLATILE SURFACTANTS (71) Applicant: The Regents of the University of California, Oakland, CA (US)

(72) Inventors: Robert M. Glaeser, Berkeley, CA (US); Bong-Gyoon Han, Castro Valley, CA (US)

(73) Assignee: The Regents of the University of California, Oakland, CA (US)

( * ) Notice: Subject to any disclaimer, the term of this patent is extended or adjusted under 35 U.S.C. 154(b) by 143 days.

(21) Appl. No.: 15/194,777

(22) Filed: Jun. 28, 2016

(65) Prior Publication Data
US 2017/0004953 A1   Jan. 5, 2017

Related U.S. Application Data (60) Provisional application No. 62/186,709, filed on Jun. 30, 2015.

(51) Int. Cl.
*G01N 1/42* (2006.01)
*G01N 1/40* (2006.01)

(52) U.S. Cl.
CPC ........... *G01N 1/42* (2013.01); *G01N 1/40* (2013.01); *G01N 1/405* (2013.01); *G01N 2001/4061* (2013.01)

(58) Field of Classification Search
None
See application file for complete search history.

(56) References Cited

U.S. PATENT DOCUMENTS

| | | | | |
|---|---|---|---|---|
| 2003/0080143 A1* | 5/2003 | Kale | ...................... | B01L 3/0262 222/1 |
| 2005/0230636 A1* | 10/2005 | Tanaka | ..................... | H01J 37/20 250/440.11 |
| 2006/0169918 A1* | 8/2006 | Ueno | ........................ | G01N 1/42 250/443.1 |
| 2009/0173882 A1* | 7/2009 | Kuwabata | ............ | G01N 23/225 250/307 |
| 2011/0006208 A1* | 1/2011 | Freitag | ................ | G01N 23/2251 250/307 |
| 2012/0120226 A1* | 5/2012 | de Jonge | ............ | G01N 23/2204 348/80 |

(Continued)

OTHER PUBLICATIONS

Robert M. Glaeser, et al., "Factors that Influence the Formation and Stability of Thin, Cryo-EM Specimens," Biophysical Journal, vol. 110, Feb. 2016, 749-755.

(Continued)

*Primary Examiner* — James Choi (57) ABSTRACT

This disclosure provides systems, methods, and apparatus related to the preparation of electron microscopy specimens. In one aspect, a method includes providing an electron microscopy grid. An aqueous suspension including an electron microscopy sample is deposited on the electron microscopy grid. A portion of the aqueous suspension is removed from the electron microscopy grid. A volatile surfactant is contacted to the aqueous suspension. A thickness of aqueous suspension is allowed to decrease over a period of time. The aqueous suspension is then frozen.

20 Claims, 6 Drawing Sheets

(56) References Cited

U.S. PATENT DOCUMENTS

2014/0360286 A1* 12/2014 Carragher ............ H01J 37/261
  73/863.11

OTHER PUBLICATIONS

Adrain, M., et al. 1984. Cryo-electron microscopy of viruses. Nature. 308:32-36.

Dubochet J., et al. 1985. Cryo-electron microscopy of vitrified biological specimens. Trends Biochem. Sci. 10:143-146.

Dobro, M. J., et al. 2010. Plunge freezing for electron cryomicroscopy. Methods Enzymol. 481:63-82.

Parsegian, V. A., et al. 2011. Hydration forces: observations, explanations, expectations, questions. Curr. Opin. Colloid Interface Sci. 16:618-624.

Liao, M., et al. 2013. Structure of the TRPV1 ion channel determined by electron cryo-microscopy. Nature. 504:107-112.

Kenworthy, A. K., et al. 1995. Range and magnitude of the steric pressure between bilayers containing phospholipids with covalently attached poly(ethylene glycol). Biophys. J. 68:1921-1936.

Jaffe, J. S., et al. 1984. Preparation of frozen-hydrated specimens for high resolution electron microscopy. Ultramicroscopy. 13:373-377.

Taylor, K. A., et al. 1973. Hydrophilic support films of controlled thickness and composition. Rev. Sci. Instrum. 44:1546-1547.

Chang, C. F., et al. 1985. The fatty-acid monolayer technique for preparing frozen-hydrated specimens. J. Electron Microsc. Tech. 2:59-65.

Hayward, S. B., et al. 1978. Molecular orientation of bacteriorhodopsin within the purple membrane of Halobacterium halobium. Proc. Natl. Acad. Sci. USA. 75:4320-4324.

Tribet, C., et al. 1996. Amphipols: polymers that keep membrane proteins soluble in aqueous solutions. Proc. Natl. Acad. Sci. USA. 93:15047-15050.

Frederik, P. M., et al. 1989. Phospholipid, nature's own slide and cover slip for cryo-electron microscopy. J. Microsc. 153:81-92.

* cited by examiner

METHODS AND APPARATUS FOR PREPARING AQUEOUS SPECIMENS FOR ELECTRON MICROSCOPY USING VOLATILE SURFACTANTS

RELATED APPLICATIONS

This application claims priority to U.S. Provisional Patent Application Ser. No. 62/186,709, filed Jun. 30, 2015, which is herein incorporated by reference.

STATEMENT OF GOVERNMENT SUPPORT

This invention was made with government support under Contract No. DE-AC02-05CH11231 awarded by the U.S. Department of Energy and under Grant No. GM083039 from the National Institutes of Health. The government has certain rights in this invention.

TECHNICAL FIELD

This disclosure relates generally to the preparation of specimens for electron microscopy.

BACKGROUND

A method to prepare macromolecular particles embedded in vitreous ice was initially described in Adrian et al., 1984 and Dubochet et al., 1985, and since then thin samples have continued to be made by blotting excess liquid from electron microscopy grids with filter paper. In many cases, it is likely that evaporation plays a significant role in thinning the sample, and often this has a detrimental effect on the structure of the specimen. The use of computerized control of key parameters (such as, for example, the ambient temperature and humidity, the blotting pressure and duration, and the interval between blotting and final vitrification) has improved the sophistication and the reproducibility with which cryo-specimens can be prepared. Even so, the results still remain less consistent from trial to trial and over the entire area of an electron microscopy grid. In particular, preparation of specimens at a desired thickness of ~30 nanometers (nm) to 50 nm remains unreliable.

Achieving specimen thicknesses well below ~100 nm becomes increasingly important as the resolution of cryo-EM images is increased (Agard et al., 2014). This is because a single image may contain particles located at different focal heights if the vitrified ice is significantly thicker than the particle size. Merging such data leads to an unwanted envelope function (Jensen, 2001) that is equivalent to the one produced by varying the focus of the objective lens by the same amount.

Even if all particles are tethered at a common Z-height, as is possible when using a continuous support film, an ice-film thickness significantly greater than the size of the particle will necessarily cause an increase in the fraction of electrons that are inelastically scattered. This is undesirable because any unnecessary increase in the fraction of inelastically scattered electrons leads to a corresponding loss of useful signal in the image.

SUMMARY

One innovative aspect of the subject matter described in this disclosure can be implemented in a method including providing an electron microscopy grid. An aqueous suspension including an electron microscopy sample is deposited on the electron microscopy grid. A portion of the aqueous suspension is removed from the electron microscopy grid. A volatile surfactant is contacted to the aqueous suspension. A thickness of aqueous suspension is allowed to decrease over a period of time. The aqueous suspension is then frozen.

Another innovative aspect of the subject matter described in this disclosure can be implemented in an apparatus including a chamber, the chamber defining a plurality of ports, a rod disposed in the chamber, and a sample holder attached to the rod. The apparatus is operable to perform a method comprising receiving an electron microscopy grid in the sample holder, receiving a deposition of an aqueous suspension including an electron microscopy sample on the electron microscopy grid, receiving an absorbent material to remove a portion of the aqueous suspension from the electron microscopy grid, receiving a volatile surfactant to contact the aqueous suspension, allowing a thickness of aqueous suspension to decrease over a period of time, and freezing the aqueous suspension.

Details of one or more embodiments of the subject matter described in this specification are set forth in the accompanying drawings and the description below. Other features, aspects, and advantages will become apparent from the description, the drawings, and the claims. Note that the relative dimensions of the following figures may not be drawn to scale.

DETAILED DESCRIPTION

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention. Various techniques and mechanisms of the present invention will sometimes be described in singular form for clarity. However, it should be noted that some embodiments include multiple iterations of a technique or multiple instantiations of a mechanism unless noted otherwise.

The terms "about" or "approximate" and the like are synonymous and are used to indicate that the value modified by the term has an understood range associated with it, where the range can be ±20%, ±15%, ±10%, ±5%, or ±1%. The term "substantially" is used to indicate that a value is close to a targeted value, where close can mean, for example, the value is within 80% of the targeted value, within 90% of the targeted value, within 95% of the targeted value, or within 99% of the targeted value.

In current practice in the preparation of some electron microscopy samples for transmission electron microscopy (TEM), a small volume of aqueous suspension (e.g., about 3 microliters) is applied to a hydrophilic electron microscopy grid, excess liquid is blotted away with filter paper, and the grid is plunged into liquid ethane to vitrify the aqueous solvent. A specific specimen thickness can be achieved by varying several parameters, including the temperature, the relative humidity, the blotting pressure and time, and the time that one waits between blotting the grid and plunging the grid into liquid ethane. In this approach, the thickness usually varies over the area of a single electron microscopy grid between regions that have no vitreous ice disposed thereon to regions that have vitreous ice disposed thereon that is too thick for electron microscopy. In some cases, it is likely that evaporation plays a role in thinning the sample, and often this has a detrimental effect on the structure of the specimen.

Some implementations of the methods and apparatus described herein can be used to create a uniformly thin film of an aqueous specimen intended for use in transmission electron microscopy. The thickness of the specimens can be controlled. For example, the thickness of a specimen may be about 30 nanometers (nm) or 100 nm. Once prepared, such specimens will be frozen rapidly enough to vitrify the aqueous solvent.

Figure 1A:
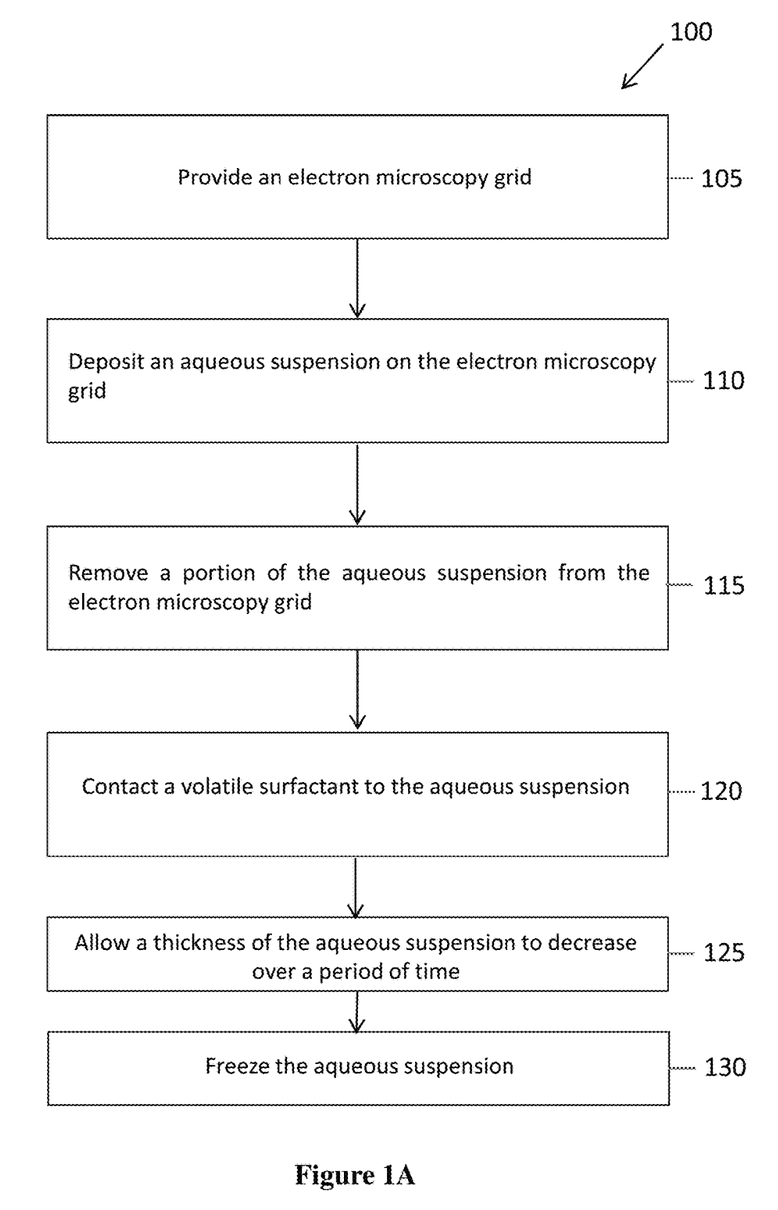
FIG. 1A shows an example of a flow diagram illustrating a method of preparing an electron microscopy grid.

FIG. 1A shows an example of a flow diagram illustrating a method of preparing an electron microscopy grid. Starting at block 105 of a method 100, an electron microscopy grid is provided. An electron microscopy grid is a grid upon which a sample can be placed. The grid can be placed in an electron microscopy specimen stage that can be inserted into the electron microscope. Electron microscopy grids are generally used in transmission electron microscopy (TEM).

An electron microscopy grid can be made of a number of materials or a combination or alloy of such materials. In some embodiments, the electron microscopy grid comprises gold, molybdenum, titanium, or copper. It is believed that molybdenum has a thermal expansion that is matched with carbon, which may desirable in some cases. In some embodiments, an electron microscopy grid is an about 3 mm diameter disc (e.g., 3.05 mm diameter) that has a thickness and mesh size ranging from about 3 microns to 100 microns. In some embodiments, an electron microscopy grid has a thickness of about 30 microns and a mesh size of about 100 microns.

Figure 1B:
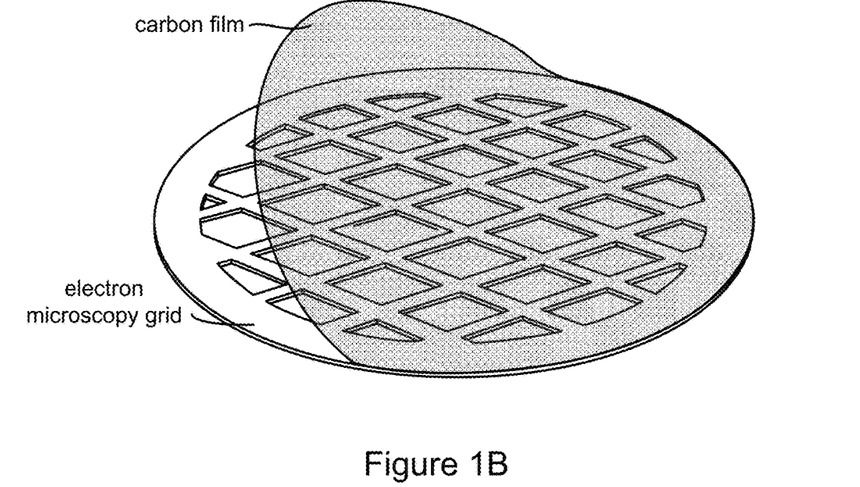
FIG. 1B shows an example of a schematic illustration of an electron microscopy grid that may be used in the method 100.

In some embodiments, the electron microscopy grid comprises a first surface and a second surface, and the first surface of the electron microscopy grid has a carbon film disposed thereon. In some embodiments, the carbon film is hydrophilic. In some embodiments, a carbon film can be made to be hydrophilic by exposure to a glow discharge. In some embodiments, the carbon film has a thickness of about 10 nm to 25 nm, or about 12 nm. In some embodiments, the carbon film is a chemically derivatized thin carbon. In some embodiments, the carbon film is a continuous carbon film. In some embodiments, the carbon film is a holey carbon film. A holey carbon film differs from a continuous carbon film in that a holey carbon film has holes defined in the carbon film. In some embodiments, the holes in the holey carbon film have a specific size. In some embodiments, the holes in the holey carbon film have a cross-sectional dimension of about 1 micron, about 2 microns, or about 1 micron to 2 microns. For example, when the holes in the holey carbon film are circular, the holes may have a diameter of about 1 micron, about 2 microns, or about 1 micron to 2 microns. In some embodiments, the electron microscopy grid is an affinity grid that has a lipid layer spanning a holey carbon film. FIG. 1B shows an example of a schematic illustration of an electron microscopy grid that may be used in the method 100. The electron microscopy grid shown in FIG. 1B comprises a disk of metal defining a mesh and a carbon film disposed on a first side of the disk of metal.

At block 110, an aqueous suspension is deposited on the electron microscopy grid. An aqueous suspension is generally considered to be a heterogeneous mixture containing solid particles that are suspended in an aqueous solvent (i.e., water). In some embodiments, the aqueous suspension contains the sample or specimen that is to be observed in the electron microscope. For example, the aqueous suspension may include a plurality of samples, with all of the samples being substantially similar to one another. For example, the plurality of samples may comprise a specific type of a biological macromolecule. In some embodiments, a volume of aqueous suspension deposited on an electron microscopy grid is about 3 microliters or less. In some embodiments, the electron microscopy grid includes a carbon film on one surface of the electron microscopy grid, and the aqueous suspension is deposited on the carbon film.

At block 115, a portion of the aqueous suspension is removed from the electron microscopy grid. In some embodiments, the portion of the aqueous suspension that is removed from the electron microscopy grid is excess aqueous suspension. In some embodiments, the portion of the aqueous suspension is removed by contacting an edge of the electron microscopy grid with an absorbent material. For example, the absorbent material may be filter paper. In some embodiments, the portion of the aqueous suspension is removed by contacting a face (e.g., the surface onto which the aqueous suspension was deposited) of the electron microscopy grid with an absorbent material. In some embodiments, after removing the portion of the aqueous suspension and before block 120, a thickness of the aqueous suspension on the electron microscopy grid is about 10 microns, about 100 microns, or about 10 microns to 100 microns.

At block 120, a volatile surfactant is contacted to the aqueous suspension. In some embodiments, the volatile surfactant is selected from a group consisting of chloroform and nonafluorobutyl methyl ether. In some embodiments, the volatile surfactant is contacted to the aqueous suspension using a capillary (e.g., a pipette tip). In some embodiments, the volatile surfactant is contacted to the aqueous suspension using a microfluidic device. The microfluidic device may be an inkjet printer which delivers small droplets or vapor of the volatile surfactant onto the aqueous suspension on the electron microscopy grid.

In some embodiments, the volatile surfactant is contacted to the aqueous suspension by exposing the aqueous suspension to vapor of the volatile surfactant. For example, the volatile surfactant may be brought close to but not touching the aqueous solution. This can serve as a point source of volatile surfactant. The purpose of the volatile surfactant vapor is for it to adsorb locally to the air-water interface of the liquid film of the aqueous suspension in order to establish a gradient of surface tensions across the face of the electron microscopy grid. This gradient of surface tension produces a uniform thinning in the area closest to the point source of the volatile surfactant by the process known as the Marangoni effect. The gradient in the surface tension drives fluid flow to the periphery of the electron microscopy grid, where the excess aqueous suspension can be blotted away in order to prevent its return later in the method 100. In some embodiments, the volatile surfactant is in a liquid state when it is contacted to the aqueous suspension.

In some embodiments, a non-volatile surfactant is contacted to the aqueous suspension at the same time that the volatile surfactant is contacted to the aqueous suspension. For example, in some embodiments, a non-volatile surfactant is dissolved in the volatile surfactant. In some embodiments, the volatile surfactant with a non-volatile surfactant dissolved therein is in a liquid state when it is contacted to the aqueous suspension. In some embodiments, the non-volatile surfactant serves as a molecular cover slip to stabilize the aqueous suspension at a specific thickness value prior to freezing at block 130. In other words, the non-volatile surfactant can leave a thin surfactant layer permanently on the aqueous suspension after it has been thinned by Marangoni flow. In some embodiments, the non-volatile surfactant comprises other means of controlling the disjoining pressure and thereby controlling the thickness of aqueous suspension prior to freezing at block 130. In some embodiments, the non-volatile surfactant includes phospholipid vesicles, such as dimyristoyl phosphatidyl choline (DMPC) vesicles (Frederik et al., 1989), for example. In some embodiments, the non-volatile surfactant includes phospholipid vesicles at a specific concentration to produce a preference for sheets over intact vesicles. In some embodiments, the non-volatile surfactant includes amphipols or a number of relatively low-molecular weight proteins, such as cytochrome C, beta-casein, or combinations thereof, for example, which are known for their ability to stabilize bubbles.

At block 125, a thickness of aqueous suspension is allowed to decrease over a period of time. In some embodiments, the period of time is about 1 second to 300 seconds. In some embodiments, the thickness of aqueous suspension on the electron microscopy grid is allowed to decrease to about 100 nm or less. In some embodiments, the thickness of aqueous suspension on the electron microscopy grid is allowed to decrease to about 40 nm or less. In some embodiments, the thickness of aqueous suspension on the electron microscopy grid is allowed to decrease to about 30 nm.

At block 130, the aqueous suspension is frozen. In some embodiments, the aqueous suspension is frozen when it is in contact with the electron microscopy grid. For example, the aqueous suspension may be frozen when the thickness of the aqueous suspension on the electron microscopy grid has reached a specific thickness. In some embodiments, the aqueous suspension is frozen by contacting the electron microscopy grid to liquid ethane. Contacting includes immersing the electron microscopy grid in liquid ethane.

In some embodiments, the operations of blocks 110, 115, 120, and 125 are performed at a specific temperature and a specific relative humidity. For example, the specific temperature may be about 0° C. to 40° C. The specific relative humidity may be about 50% to 100%.

Another aspect of the described implementations is an apparatus configured to accomplish the methods described herein. A suitable apparatus includes hardware for accomplishing the process operations and a system controller having instructions for controlling process operations in accordance with the present invention. Hardware for accomplishing the process operations includes a chamber. The system controller will generally include one or more memory devices and one or more processors configured to execute some or all the instructions so that the apparatus will perform a method in accordance with the present invention. Machine-readable media containing instructions for controlling process operations in accordance with the present invention may be coupled to the system controller. In some embodiments, the system controller instructs a robotic device or devices associated with the apparatus that perform some or all of the operations of a method in accordance with the present invention. In some embodiments, a human operator, using the apparatus, performs some or all of the operations of a method in accordance with the present invention.

Figure 1C:
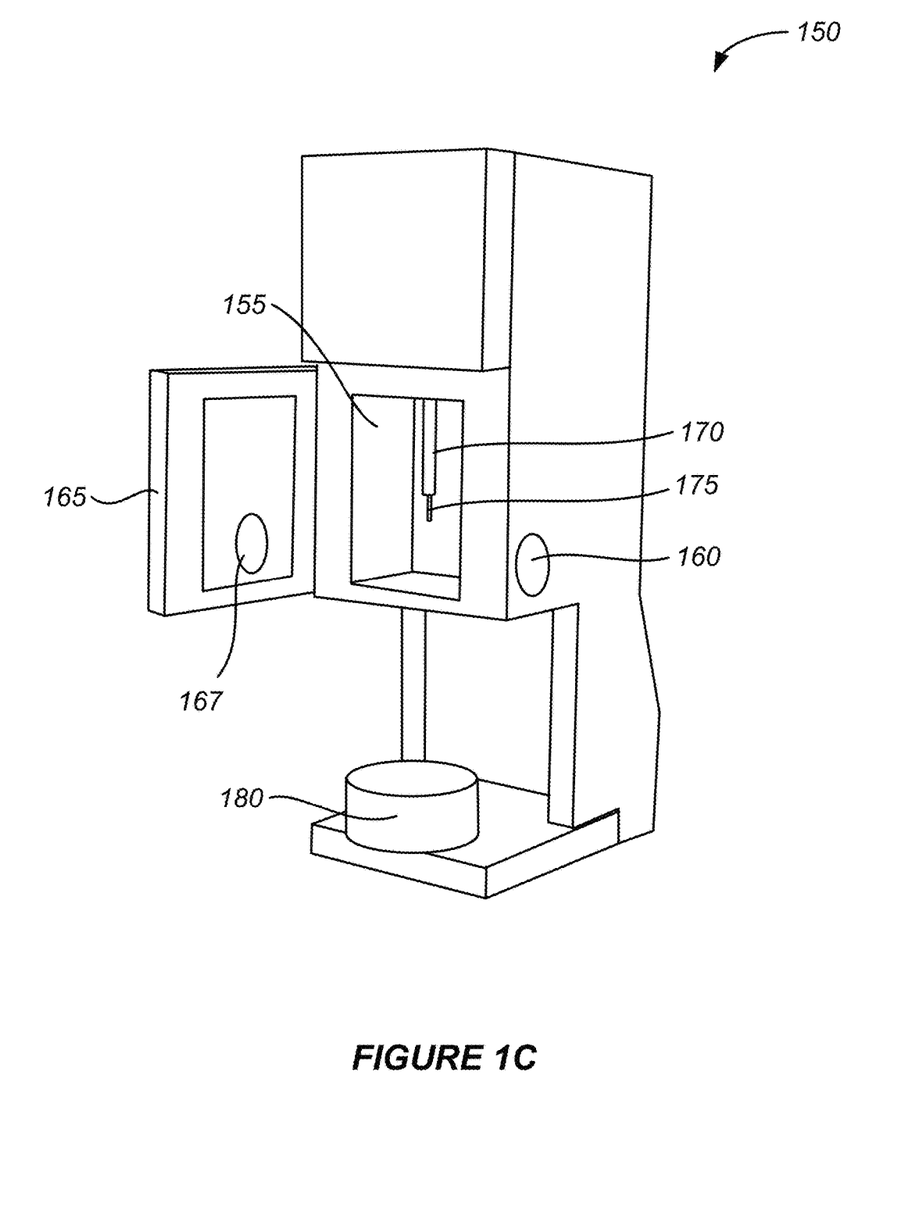
FIGS. 1C and 1D show examples of schematic illustrations of an electron microscopy grid preparation apparatus.
Figure 1D:
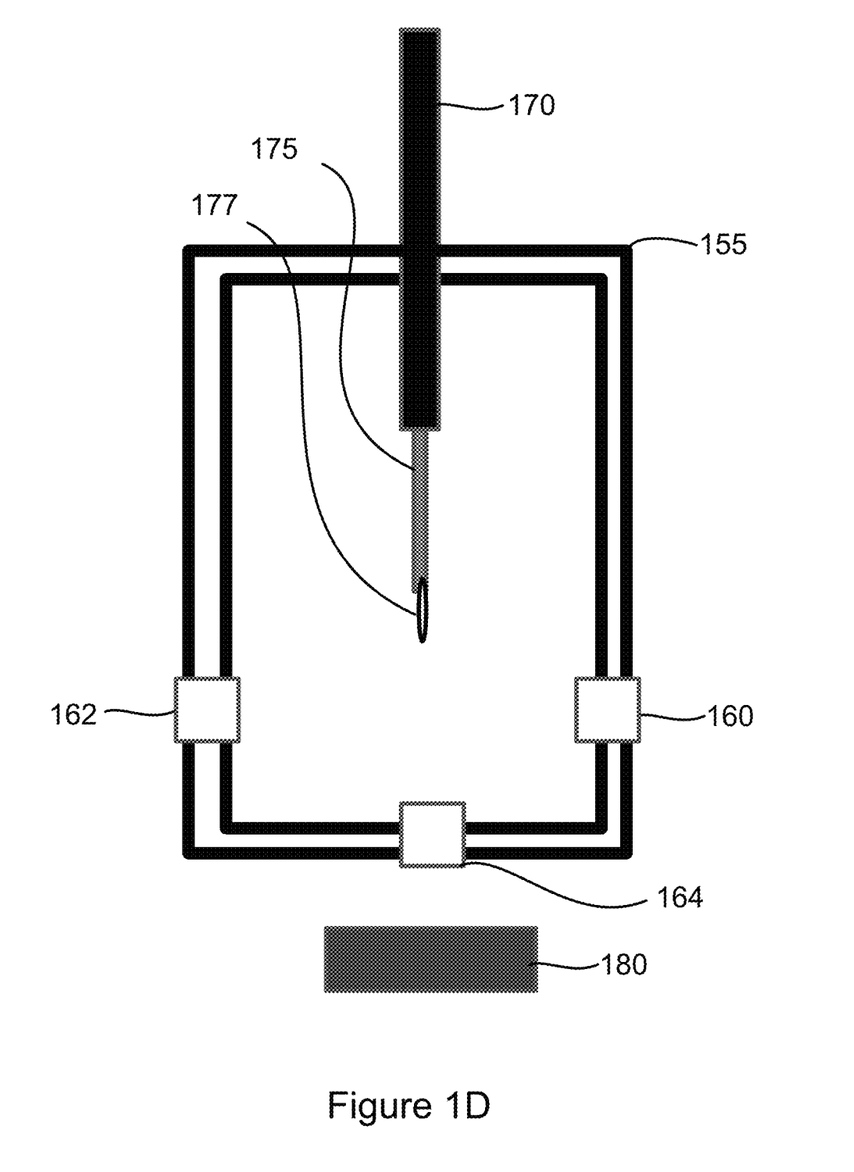

FIGS. 1C and 1D show examples of schematic illustrations of an electron microscopy grid preparation apparatus. As shown in FIG. 1C, an electron microscopy grid preparation apparatus 150 includes a chamber 155. FIG. 1D shows an example of a cross-sectional schematic illustration of the chamber 155. A door 165 allows access to the chamber 155. When the door 165 is closed, the temperature and the relative humidity in the chamber 155 may be controlled. The chamber 155 defines a first port 160, a second port 162, and a third port 164. The door 165 defines a port 167. The ports 160, 162, 164 and 167 may be open or closed, depending on the operations being performed in the chamber 155. Also disposed in the chamber 155 is a rod 170 on which a sample holder 175 is mounted. The sample holder 175 is operable to hold an electron microscopy grid 177. In some embodiments, the sample holder 175 comprises tweezers. The apparatus 150 also includes a dewar 180. The dewar 180 is operable to hold or contain a cryogen. In some embodiments, the apparatus 150 further comprises a depositing mechanism (not shown), a removing mechanism (not shown), and a contacting mechanism (not shown).

The apparatus 150 may perform the method 100 and variations of the method 100 described herein. In some embodiments, the apparatus 150 is operable to perform a method including receiving an electron microscopy grid 177 in the sample holder 175. For example, the sample holder may comprise tweezers and the tweezers may be in an open position. When an electron microscopy grid 177 is positioned between the tweezers, the tweezers may switch to a closed position in which the tweezers hold the electron microscopy grid. The electron microscopy grid 177 may be positioned in the sample holder 175 through the opening in the chamber 155 when the door 165 is in an open position, In some embodiments, a deposition of an aqueous suspension including an electron microscopy sample is received on the electron microscopy grid. For example, a device (e.g., a pipette) or a depositing mechanism may be inserted through the port 160, 162, or 167 to deposit the aqueous suspension.

In some embodiments, an absorbent material is received to remove a portion of the aqueous suspension from the electron microscopy grid. For example, the absorbent material may be inserted through the port 160, 162, or 167 to remove a portion of the aqueous suspension from the electron microscopy grid. The absorbent material may be attached to or part of a removing mechanism. An edge of the electron microscopy grid or a face of the electron microscopy grid may be contacted with the absorbent material to remove the portion of the aqueous suspension.

In some embodiments, a volatile surfactant is received to contact the aqueous suspension. For example, a device (e.g., a pipette) or contacting mechanism may be inserted through the port 160, 162, or 167 to contact the aqueous suspension with the volatile surfactant.

In some embodiments, a thickness of aqueous suspension is allowed to decrease over a period of time. In some embodiments, the period of time is about 1 second to 300 seconds. In some embodiments, the thickness of aqueous suspension on the electron microscopy grid is allowed to decrease to about 100 nm or less.

In some embodiments, the aqueous suspension is frozen. For example, when the thickness of the aqueous suspension has reached a specific thickness, the electron microscopy grid may contacted with a cryogen. In some embodiments, the aqueous suspension is frozen by the rod 170 lowering the electron microscopy grid 177 through the port 164. The electron microscopy grid 177 is then contacted or immersed in a cryogen (e.g., liquid ethane) held in the dewar 180. In some embodiments, the apparatus 150 includes a mechanism operable to move the electron microscopy grid from the chamber 155 to the cryogen held in the dewar 180. In some embodiments, the aqueous suspension is frozen by contacting the aqueous suspension with a cryogen provided through the ports 160, 162, or 167 via a contacting mechanism.

In some embodiments, a method is performed with the apparatus 150 with the atmosphere in the chamber 155 being maintained at a specific temperature and a specific relative humidity. The specific temperature and the specific relative humidity may be maintained in the chamber 155 by the system controller after the electron microcopy grid 177 is received in the sample holder 175. In some embodiments, the specific temperature is about 0° C. to 40° C. In some embodiments, the specific relative humidity is about 50% to 100%.

In some embodiments, a reflected light microscope device (not shown) is attached to or part of the door 165 of the apparatus 150. In some embodiments, the reflected light microscope device operates in an epi-illumination mode (i.e., illumination and detection occurring from one side of the sample). The reflected light microscope device may be used by a human operator to perform some or all of the operations of a method in accordance with the present invention.

The apparatus 150 may be similar to a Vitrobot (FEI, Inc., Hillsboro, Oreg.). Components of a Vitrobot may be modified, replaced, and/or removed to perform the method 100. Other apparatus that possibly could be used to perform the method 100 include the Leica EM GP (Leica Microsystems Inc., Buffalo Grove, Ill.) and the Cryoplunge 3 System (Gatan, Inc., Pleasanton, Calif.).

EXAMPLE

The following examples are intended to be examples of the embodiments disclosed herein, and are not intended to be limiting.

Poor consistency of the ice thickness from one area of a cryo-electron microscope (cryo-EM) specimen grid to another, from one grid to the next, and from one type of specimen to another, motivates a reconsideration of how to best prepare suitably thin specimens. Here we discuss related topics of wetting, thinning, and stability against dewetting of aqueous films spread over a hydrophilic substrate. We then suggest that the importance of there being a surfactant monolayer at the air-water interface of thin, cryo-EM specimens has been largely under-appreciated. In fact, a surfactant layer of uncontrolled composition and surface pressure can hardly be avoided during standard cryo-EM specimen preparation. We thus suggest that better control over the composition and properties of the surfactant layer may result in more reliable production of cryo-EM specimens with a specified thickness.

In this example, we considered the case in which the support film on the electron microscopy (EM) grid is continuous and hydrophilic. This is expected to provide a good model for describing what happens when cryo-EM samples are prepared on a continuous, glow-discharge-treated carbon film. There will be additional effects, of course, when holey carbon films are used. Even in the case of holey carbon films, however, we believe the basic principles described herein will still apply to the formation and the stability of thin aqueous films.

We first present background about the wetting of surfaces (e.g., substrates) under equilibrium conditions. We also address the question of the maximum amount of liquid that can be removed when a grid is drained (e.g., wicked) from an edge, and why it is necessary to press the filter paper directly on the face of the grid if there is to be any chance of producing a suitably thin sample.

Then we explain the fact that uniformly thin films of pure water, in the shape of a flat pancake, for example, are unstable with respect to dewetting the substrate. Dewetting results in the formation of puddles whose thickness is determined by the very small, but still finite contact angle, and by the size (e.g., diameter/volume) of the puddle(s).

We then go on to present the fact that a surfactant monolayer can act to suppress the thickness fluctuations that nucleate dewetting within the interior of, as opposed to at the edge of, a uniformly thin pancake. When such internal nucleation events are suppressed, a uniformly thin aqueous film may become metastable, as are soap bubbles. This means, in the context of making cryo-EM specimens, that the presence of a surfactant monolayer at the air-water interface can be desirable.

We further present the fact that additional interactions emerge between apposed interfaces as the separation between them becomes very small. The thickness of a thin liquid film, when stabilized by a surfactant monolayer, for example, is ultimately determined by the range and magnitude of these interfacial interactions. Thus, by controlling the chemical makeup of this surfactant monolayer, it may be possible to engineer a local minimum in the total energy of the system at a thickness that is useful for a particular cryo-EM specimen.

Finally, we present some of the ways in which a surfactant monolayer of defined composition might be intentionally applied to the air-water interface during the preparation of cryo-EM grids. We include a description of work in which we observed that one such method, delivery of a phospholipid dissolved in chloroform, is accompanied by thinning of an aqueous puddle even before there is direct, liquid-liquid contact. This example of the Marangoni effect, well-known in other applications (e.g., such as the drying of silicon wafers), has the potential to serve as an alternative to blotting with filter paper, as a way to produce thin aqueous films.

The Initial Formation of Thin Aqueous Films on EM Grids. A small amount of water that is placed on an extended, clean surface, such as freshly cleaved mica, normally forms a puddle whose contact angle, θ, with the substrate satisfies the equation attributed to Young, 1805:

$$\cos\theta = \frac{\gamma_{SG} - \gamma_{SL}}{\gamma_{LG}}, \qquad \text{Equation 1}$$

where $\gamma_{SG}$, $\gamma_{SL}$, and $\gamma_{LG}$ are the surface tensions (i.e., surface energies) for the solid-gas, solid-liquid, and liquid-gas interfaces, respectively. The surface tension of water at the water-air interface is approximately 70 mN/m. The other two values of surface tension are necessarily dependent on the nature of the solid substrate.

Figure 2:
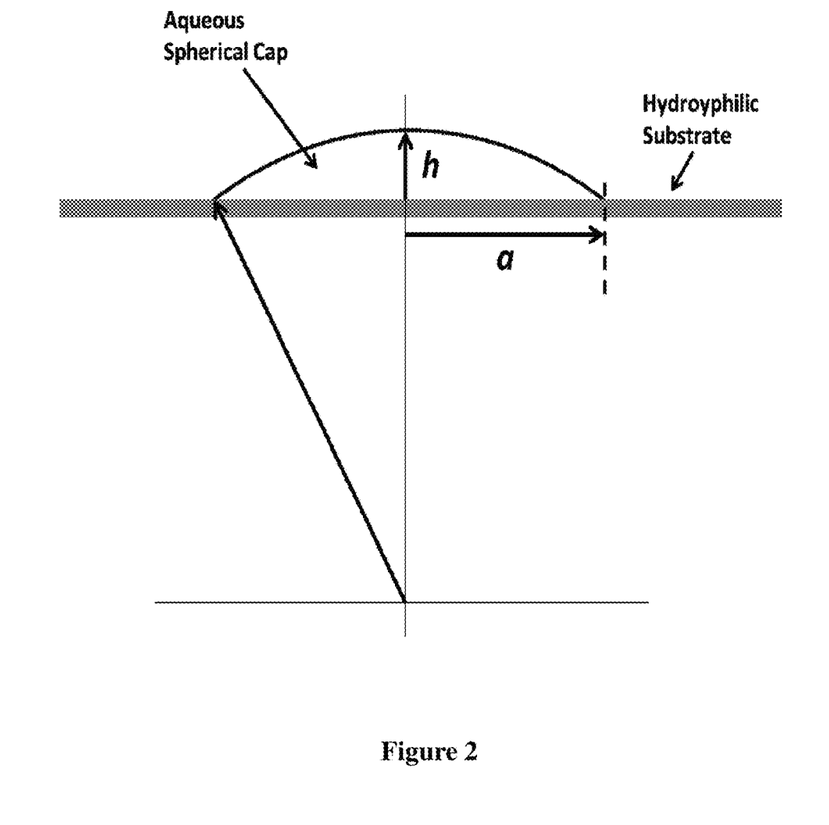
FIG. 2 is an example illustrating the side view of the equilibrium shape in which the spherical cap refers to the top-most portion of a sphere. For completeness, the radius of the sphere, and its center, are shown below the plane of the hydrophilic substrate. In top view (not shown), the perimeter of the cap would be a circle of radius a. The thickness of the spherical cap (at the center of the plano-concave lens), h, is given by Equation 3, described below.

When the thickness of a liquid puddle is small enough, the effect that gravity has on its shape can be ignored. In this case the equilibrium shape is that of the top-most portion (i.e., the cap) of a sphere. (See FIG. 2 for an illustration.) The length scale below which the influence of gravity is negligible is known as the capillary length, $\lambda_c$, and it is given by $$\lambda_C = \sqrt{\frac{\gamma_{LG}}{\rho g}}, \qquad \text{Equation 2}$$

where ρ is the density of water and g is the gravitational acceleration. For pure water, the capillary length is ~2 mm at 1 g. As a practical illustration, little if any change in the shape of a 3 μl drop can be noticed when a 3 mm electron microscopy grid is held in either a horizontal or vertical orientation.

When the available area is not limiting, the diameter (e.g., puddle size) of a water drop, and its thickness at the center of the drop, are determined by the volume of liquid placed on the hydrophilic surface. The puddle thickness, h, is of special interest to us, and it can be expressed as a function of the contact angle and the radius, α, of the puddle:

$$h = \frac{a}{\sin\theta}(1 - \cos\theta) \approx \frac{a\theta}{2}, \qquad \text{Equation 3}$$

the latter approximation applying when the contact angle is small.

When the available surface area is limiting, as it is when excess sample is placed on an EM grid, the initial droplet can be thicker than the value described in Equation 3, since the water cannot spread beyond the edge of the grid. Nevertheless, the droplet will still form a spherical cap, as long as the thickness of the drop is smaller than the capillary length.

When excess sample is first applied to a hydrophilic grid, the available area will be limiting and thus the height of the spherical cap will generally be greater than what is specified in Equation 3. In this case, excess liquid can be drained (e.g., wicked) away by touching the edge of the EM grid with filter paper. Draining will stop at the point where the contact angle at the rim of the spherical cap is determined by how hydrophilic the surface is, rather than by how much area is available. The volume, V, of liquid that remains after draining can be expressed in terms of the radius,α, of the puddle that remains, which should be equal in size to the radius of the EM grid, and the thickness, h, of the puddle $$V = \frac{\pi h}{6}(3a^2 + h^2) \approx \frac{\pi}{4}a^3\theta, \qquad \text{Equation 4}$$

the latter approximation again applying when the contact angle is small, thus allowing us to substitute the thickness parameter by the expression on the far right of Equation 3.

As stated in Equation 3, the thickness of the puddle at the middle of the spherical cap is proportional to the contact angle when the latter is small. If the grid is made hydrophilic by exposure to a glow discharge, the contact angle is, in fact, so small that it is not practical to measure it visually. The volume of water that remains after wicking can be estimated gravimetrically, however. In our hands, this volume is at least 20 nl (as measured with a microbalance). If the radius is assumed to be 1.5 mm (i.e., the size of the entire EM grid), this volume corresponds to the contact angle (expressed in Equation 4) being approximately 0.4 degrees. As a result, the thickness at the middle (expressed in Equation 3) is thus estimated to be approximately 6 μm or more.

An important conclusion is that blotting excess liquid from the edge of a vertically held EM grid does not produce a film of aqueous sample that is thin enough to use as a cryo-EM specimen. Furthermore, blotting from the bottom of the grid cannot result in a significant gradient of thickness from the top to the bottom of the grid, as has sometimes been stated (Frederik et al., 1989).

On the other hand, areas of thin ice, usually accompanied by other areas that are too thick to be used, are routinely obtained by pressing filter paper to the face of the grid. Blotting against the face of a grid will remove more water than blotting from the edge because the puddle of water is mechanically flattened as well as being wicked away simultaneously at many points. The hope is that such face blotting initially leaves a uniformly thin aqueous film (e.g., a pancake) covering at least some parts, if not all, of the grid. It is perhaps impossible to observe, prior to freezing, whether that really happens. Nevertheless, supposing that a uniformly thin pancake actually is produced, whose thickness is less than 100 nm, the next issue to review is how stable such a liquid film is likely to be.

Uniformly Thin Films of Pure Water are Inherently Unstable. While it is possible to briefly spread (e.g., flatten or smear) a small volume of water into a thin pancake, doing so means that the surface-to-volume ratio is greater than if the same volume adopted the shape of a spherical cap. If the thickness of the flattened volume is still relatively large (e.g., greater than ~100 nm, as we will explain below), one can expect the spread film of water to dewet the substrate only at the outer rim of the pancake, quickly contracting the entire volume of water to the original, equilibrium shape. It is only if the same volume of water is spread into a much thinner pancake that one can expect dewetting (discussed in chapter 7 of de Gennes et al., 2004), to occur at one or more points within the film as well as at the outer edges. Note that, as a consequence of dewetting, departures in puddle shapes from the ideal spherical caps imagined above can be attributed to inhomogeneities or defects on the substrate that are able to pin the contact line (i.e., where solid, gas, and liquid meet).

It may seem surprising that van der Waals forces are responsible for the internal dewetting events that occur when a film of liquid is still much thicker than molecular dimensions. This is nevertheless possible because the total interaction energy of molecules within a thin film of liquid, due to van der Waals forces, actually scales as the square of the film thickness (see, for example, section 2.K.2. of Berg 2010), even though the interaction energy between any pair of molecules scales as the sixth power of their separation. As a result, once a liquid film becomes thinner than a certain value, generally believed to be ~100 nm (Vrij, 1966; Wyart and Daillant, 1990), the van der Waals interaction energy of molecules within the thin film, relative to that of molecules within a thick film, decreases significantly.

Local thinning of such a liquid film thus leads to an unstable, runaway situation in which molecules in an initially thinner area move to the adjacent, thicker area, where their van der Waals energy is more favorable. There is, in fact, a second term in the van der Waals energy that also scales as the square of the thickness of the liquid film, and which again serves to drive the thickness to zero. This second term is the van der Waals attraction between the semi-infinite half spaces on either side of the liquid film—see Equation L1.2 in Parsegian, 2006. When, however, the material on either side of the liquid film is a gas at atmospheric pressure (e.g., as in our case), the low density of material makes the scaling constant (i.e., the Haymaker constant) very small compared to that of the first term discussed above.

The final result is that the thinnest areas of a liquid film act as nucleation sites for events that subsequently dewet the substrate, leaving thicker puddles (e.g., spherical caps) in equilibrium with dry areas. Restating this in simpler terms, a liquid pancake that is thinner than ~100 nm is inherently unstable with respect to dewetting at one or more points across the face of the pancake. Once dewetting begins, the same volume of liquid will minimize its surface-to-volume ratio by spontaneously coalescing into possibly quite complex patterns of wet and dry areas (Elbaum and Lipson, 1994). The practical implication, for cryo-EM specimen preparation, is that some areas of the grid are bound to become air-dried—even in the hypothetical case when the ambient humidity is so high that evaporation is not a contributing factor—while at the same time adjacent areas may be much thicker than desired.

A Surfactant Monolayer Suppresses the Thickness Fluctuations that are Required to Nucleate Dewetting. When there is a diffusible surfactant at the air-water interface, some workers believe that Marangoni flow—the bulk transfer of a liquid due to a gradient in surface tension (described in chapter 10 of (Berg, 2010), for example)—opposes any fluctuations in thickness that may nucleate the dewetting process. Although the following argument may be too simplistic, the idea is that formation of a locally thinner area (i.e., occurrence of a nascent dewetting event) is accompanied by an increase in surface area, and thus a local decrease in surface coverage by the surfactant. To the extent that this is true, local thinning would also be accompanied by a local increase in surface tension. Marangoni flow would then cause mass transfer back into the thinner area.

The suppression of thickness fluctuations (i.e., capillary waves) by a surfactant monolayer is believed to prevent nucleation of the process of rupture (i.e., dewetting) of thin, liquid layers.

Surfactant Monolayers Also Affect the Disjoining Pressure, Which Determines the Thickness of Metastable, Aqueous Films. As an aqueous film gets thinner than ~100 nm under the influence of van der Waals forces, previously ignored interactions come into play between the two, apposed interfaces. These interactions produce what is referred to as a disjoining pressure, defined as the gradient normal to the surface of the Gibbs free energy per unit area. At very close distances (e.g., generally only a few nanometers), the value of the disjoining pressure starts to change rapidly as a function of the distance. Depending upon its sign, the disjoining pressure either promotes or resists rupture (i.e., dewetting) of the thin film. It thus is important to know the physical origins of these interfacial interactions, and the extent to which they can be manipulated (e.g. by controlling the physical and chemical properties at the two, respective interfaces).

In general, polar groups at the aqueous interfaces are responsible for a hydration (i.e., solvation) force that resists complete dehydration (Parsegian and Zemb, 2011). Hydrophilic surfaces that are brought into close apposition are thus likely to maintain a gap of water between them that is at least 1 nm or possibly 2 nm thick—see section 15.8 of Israelachvili, 2011.

If the polar head groups are charged, electrostatic forces between the interfaces may also become important. Nevertheless, the range over which electrostatic forces are exerted under normal biochemical-buffer conditions is limited by shielding of the surface-charge by counter ions. The distance over which this shielding occurs depends upon the ionic strength, of course. When the ionic strength is 10 mM or more, for example, electrostatic repulsion between like-charged surfaces may not contribute much to maintaining a liquid gap between opposed interfaces, beyond what hydration (i.e., solvation) itself would ensure.

If one wants to stabilize the water film at a thickness greater than that maintained by the combination of hydration and repulsive electrostatic forces, it may be necessary to use some type of steric spacer to achieve this. This steric spacer could be the macromolecular (e.g., specimen) particles themselves, of course, or it could be even larger spacer particles that are added to the specimen. In addition, one can consider using a surfactant that has a long flexible head groups, such as polyethylene glycol chains, as a steric spacer (e.g., an entropic spring). For more on this latter possibility, see, for example, chapter 16 of Israelachvili, 2011 for a general discussion of polymer-mediated contributions to the disjoining pressure, or Kenworthy et al., 1995 for a specific example.

Possible User of Surfactant Monolayers as Electron-Transparent Cover Slips When Preparing Cryo-EM Specimens. The idea of sandwiching macromolecular specimens between a continuous carbon film which serves as an electron-transparent slide and either a fatty acid monolayer or a second carbon film (i.e., effectively a coverslip) was explored early in the development of cryo-EM specimen preparation (Chang et al., 1985; Hayward et al., 1978; Jaffe and Glaeser, 1984; Taylor and Glaeser, 1973). A retrospective in Taylor and Glaeser, 2008 describes this and other early work, which first established that high resolution information is preserved in frozen-hydrated specimens, and that adequate contrast is available in such unstained specimens. The attempt to use an electron-transparent coverslip was not pursued further, however, when the far simpler technique of blotting excess liquid with filter paper (Adrian et al., 1984; Dubochet et al., 1985) proved to be all that was needed. Now, however, as macromolecular structures are being achieved at higher and higher resolution (for example Bai et al., 2012; Campbell et al., 2015; Cao et al., 2013; Li et al., 2013; Scheres, 2014), it again becomes a priority to determine whether further improvements can be found in the methods of preparing thin specimens.

Surfactants are likely to be present in abundance. As was noted previously by Frederik et al., 1989, it seems likely that the thin (e.g., 100 nm thick or less) cryo-EM specimens that are routinely produced are covered by a monolayer of surfactant, even though no specific effort is made to ensure that it will be there. Indeed, one must take extreme measures to remove such surfactants from a sample, as the literature of surface-science makes abundantly clear. When one thinks about the steps that must be taken to prepare a clean air-water interface on a Langmuir trough, for example, the preparation of cryo-EM specimens must be considered to be a relatively dirty process.

To illustrate the point, volatile organics in the atmosphere are bound to contaminate the surface of EM grids before use, ready to spread over the air-water interface when an aqueous sample is applied. For example, Xu et al. found that such contamination accumulates on the surface of freshly cleaved mica when it is exposed to ambient atmosphere for several hours, and greatly affects the rate of evaporation of water that condenses (due to capillary action) between an AFM tip and mica (Xu et al., 1998). Any piece of laboratory equipment (e.g., tweezers, protective gloves, the plastic barrier used to prevent samples from wetting the foam on the Vitrobot paddles) will similarly be coated with a monolayer of surfactant. It has also been mentioned, but not proven experimentally, that the familiar glow-discharge process may itself generate surfactant species on the EM grid. Even macromolecules within the specimen should be regarded as potential surfactants, since proteins can easily denature and spread at an air-water interface.

One response to this situation is to simply carry on doing the sample preparation as we currently do it, and accept whatever results we normally get, variable as they may be from one grid to the next.

Another response, however, might be to reconsider applying a known, engineered coverslip to the air-water interface. Since it may be impractical to eliminate the native surfactant that is already there, however, perhaps the most that one might hope to accomplish is to overwhelm the unknown surfactant by applying excess engineered surfactant. The potential benefits of this approach might be, in turn, to produce thin samples with greater consistency, and possibly even to engineer the ice thickness to match the size of the particle being studied.

Surfactants can be added directly to the sample of interest. The addition of phospholipid vesicles to the sample of interest is a promising way to deliver a chemically-defined surfactant coverslip to the air-water interface, as was suggested by Frederik et al., 1989. This technique seems to not have been regarded by the community as being a good thing to do, perhaps because unwanted, excess liposomes remain in the thin, aqueous film. However, it seems likely that one should easily find a concentration of liposomes that would deliver enough surfactant to completely cover the air-water interface while leaving only a minimal number of intact vesicles still suspended in the bulk of the thin, vitrified sample.

The addition of detergent to the sample might be another approach, provided that the sample is not adversely affected. Many purification protocols actually include a detergent in the buffer (e.g., to prevent unwanted aggregation). The addition of detergent is also one of the standard tricks to try when a sample is found to adsorb to the air-water interface. The main shortcoming of having detergent in the sample is that the specimen may then be more sensitive to any evaporation that might occur after blotting and before freezing. In addition, some authors report that it is difficult to find areas of the grid where the ice is as thin as is desired, when there is detergent in the sample buffer.

There are many other surfactant materials that can be considered. Amphipols (Tribet et al., 1996), for example, have just recently gained attention in the context of cryo-EM of membrane proteins (Liao et al., 2013). A number of relatively low-molecular weight proteins, such as cytochrome C or beta-casein, are also known for their ability to stabilize bubbles.

Surfactant materials can be applied to the air-water interface in a volatile-solvent carrier. When doing experiments with a Langmuir trough, a surfactant of interest is normally dissolved in a volatile, organic solvent (e.g., chloroform), which is then delivered to the air-water interface. The organic solvent quickly evaporates, leaving a monolayer of the solute at the air-water interface. In principle, the same technique might be used to deliver a well-defined surfactant to the surface of an EM grid, possibly doing so after first blotting off excess liquid.

In preliminary experiments described below, we confirmed that touching a thin, aqueous puddle with phospholipid dissolved in chloroform permanently forms an apparently dry, hydrophobic patch in the center of the puddle of water. A similar, but not identical thing happens when chloroform alone is used, however. This experiment thus raises a new question. Why does the aqueous puddle become thin when touched by pure chloroform? Indeed, one can easily observe that an aqueous puddle already begins to thin as the liquid chloroform approaches the puddle, but does not yet touch it. As we explain below, it is the Marangoni effect that causes the observed thinning, and the phospholipid monolayer, if present, acts as a cover slip to stabilize the resulting, thin aqueous film.

Thinning by the Marangoni effect may even be an alternative to blotting with filter paper. As mentioned above, water experiences a bulk flow (i.e., mass transfer) whenever there is a gradient in surface tension parallel to the surface. Although this effect may be unfamiliar in the context of making cryo-EM samples, most people have seen it in the form of the tears of wine effect. Marangoni, after whom such mass-transfer effects are named, is acknowledged to be the first to publish experimental studies in 1865, and Gibbs is credited with providing the theoretical explanations in 1878.

Figure 3A:
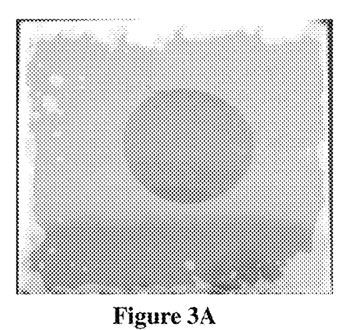
FIG. 3A-3D show examples of individual frames extracted from real-time movies in which we recorded how Marangoni flow (e.g., rather than blotting with filter paper) might be used to thin an aqueous specimen prior to vitrification.
Figure 3B:
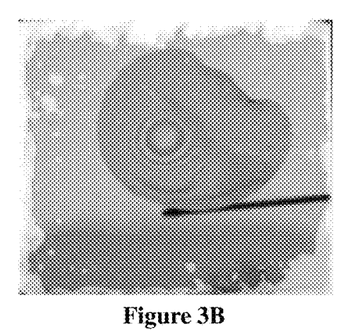

A practical demonstration of how Marangoni thinning, rather than blotting with filter paper, might be used to make thin specimens for cryo-EM is shown in FIGS. 3A-3D. FIG. 3A shows a still image of a thin puddle, approximately 1 cm in diameter, which forms when 10 µl of water is applied to the surface of freshly cleaved mica. Imperfections in the reflectance of light near the periphery of the mica are due to air gaps created by inadvertent cleavage of planes of the mica during cutting the one-inch square from stock. FIG. 3B shows that the center of the puddle can be made thinner than 100 nm by bringing a point source of chloroform vapor close to the surface. In FIG. 3B, interference fringes, centered around the point of closest approach to the aqueous puddle, are formed when a teflon syringe needle, loaded with chloroform, is brought close to the center of the puddle. This pattern of local thinning is largely reversible when the tip of the syringe is removed. On the other hand, a permanently dry area forms when liquid chloroform touches the aqueous puddle. This dry area is again wetted relatively well when a new droplet of water is applied to it, but wetting is no longer as perfect as is the case for freshly cleaved mica.

As is the case for the tears of wine phenomenon, the system shown here is in a nearly steady state rather than being at equilibrium. We suggest that the mechanism involved in establishing this steady state is that chloroform first adsorbs to the air-water interface at the point closest to the source of vapor, and in so doing lowers the surface tension there. The resulting gradient in surface tension drives mass transfer to the region of higher surface tension, carrying the monolayer of adsorbed chloroform along with the flow of water. Once removed some distance from the source of vapor, the chloroform again evaporates from the water surface, thus keeping the surface tension high in the region farther removed from the source of vapor.

Figure 3C:
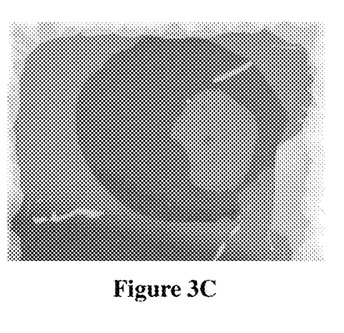
Figure 3D:
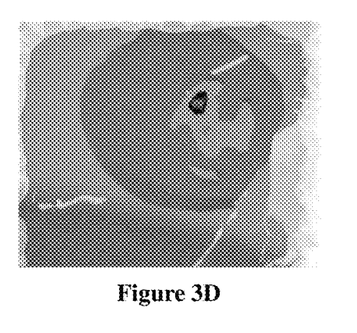

When the puddle of water is actually touched by the chloroform solution, however, phospholipid instantly spreads over the air-water interface as a coverslip. As is shown in FIG. 3C, in this case the puddle becomes permanently thinned over a large area surrounding the point of contact. The permanently dry area forms when a solution of 1 mg/ml of phospholipid in chloroform touches an aqueous puddle. Note a small amount of residue is left at the point where the transferred chloroform sat as it evaporated. Furthermore, much of the thinned area is now hydrophobic, as is seen by applying a new droplet of water, as is shown in FIG. 3D. That the dry area is largely hydrophobic is indicated by the fact that an added droplet of water does not spread. Exceptions occur when the applied droplet contacts surrounding areas of the puddle. For the reasons discussed above, we assume that a relatively thin layer of water necessarily remains between the mica and the polar headgroups of the phospholipid monolayer. This is in contrast to what happens when a puddle of water is touched by chloroform alone, in which case the dry area is still hydrophilic.

Although we have used chloroform to illustrate the Marangoni effect in FIGS. 3A-3D, we feel that a different volatile surfactant may be a better choice to use for preparing cryo-EM specimens. The reason is that the solubility of chloroform in water is quite high, ~1 percent. This means that dissolved chloroform may easily partition into the hydrophobic interior of the macromolecule of interest, and in so doing it may compromise the structure and biochemical function of the specimen. Nonafluorobutyl methyl ether might thus be a more favorable solvent to use because of its low solubility in water.

CONCLUSION

Further detail regarding the embodiments described herein can be found in Robert M. Glaeser, et al., "Factors that Influence the Formation and Stability of Thin, Cryo-EM Specimens," Biophysical Journal, Volume 110, February 2016, 749-755, which is hereby incorporated by reference.

In the foregoing specification, the invention has been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention. All publications and patents cited herein are hereby incorporated by reference.

REFERENCES

Adrian, M., J. Dubochet, J. Lepault, A. W. McDowall, 1984. Cryo-Electron Microscopy of Viruses. Nature 308, 32-36.
Agard, D., Y. Cheng, R. M. Glaeser, S. Subramaniam, 2014. Chapter Two—Single-Particle Cryo-Electron Microscopy (Cryo-EM): Progress, Challenges, and Perspectives for Further Improvement, p. 113-137, in: Hawkes, P W, (Ed.), Advances in Imaging and Electron Physics, Elsevier, Vol. Volume 185, pp. 113-137.
Bal, X. C., T. G. Martin, S. H. W. Scheres, H. Dietz, 2012. Cryo-EM structure of a 3D DNA-origami object. Proceedings of the National Academy of Sciences of the United States of America 109, 20012-20017.
Berg, J. C., 2010. An introduction to interfaces & colloids: the bridge to nanoscience. World Scientific, Hackensack, N.J.
Campbell, M. G., D. Veesler, A. Cheng, C. S. Potter, B. Carragher, 2015. 2.8 Å resolution reconstruction of the Thermoplasma acidophilum 20 S proteasome using cryo-electron microscopy.
Cao, E., M. Liao, Y. Cheng, D. Julius, 2013. TRPV1 structures in distinct conformations reveal activation mechanisms. Nature 504, 113-118.
Chang, C. F., T. Ohno, R. M. Glaeser, 1985. The fatty-acid monolayer technique for preparing frozen-hydrated specimens. Journal of Electron Microscopy Technique 2, 59-65.
de Gennes, P.-G. d., F. Brochard-Wyart, D. Quéré, 2004. Capillarity and wetting phenomena: drops, bubbles, pearls, waves. Springer, N.Y.
Dubochet, J., M. Adrian, J. Lepault, A. W. McDowall, 1985. Cryo-electron microscopy of vitrified biological specimens. Trends in Biochemical Sciences 10, 143-146.
Elbaum, M., S. G. Lipson, 1994. How does a thin wetted film dry up. Physical Review Letters 72, 3562-3565.
Frederik, P. M., M. C. A. Stuart, P. H. H. Bomans, W. M. Busing, 1989. Phospholipid, natures own slide and cover slip for cryo-electron microscopy. Journal of Microscopy-Oxford 153, 81-92.
Hayward, S. B., D. A. Grano, R. M. Glaeser, K. A. Fisher, 1978. Molecular orientation of bacteriorhodopsin within purple membrane of Halobacterium holobium. Proceedings of the National Academy of Sciences of the United States of America 75, 4320-4324.
Israelachvili, J. N., 2011. Intermolecular and surface forces. Elsevier Science Publ., San Diego, Calif.
Jaffe, J. S., R. M. Glaeser, 1984. Preparation of Frozen-Hydrated Specimens for High-Resolution Electron-Microscopy. Ultramicroscopy 13, 373-377.
Jensen, G. J., 2001. Alignment error envelopes for single particle analysis. Journal of Structural Biology 133, 143-155.
Kenworthy, A. K., K. Hristova, D. Needham, T. J. McIntosh, 1995. Range and magnitude of the steric pressure between bilayers containing phospholipids with covalently attached poly(ethylene glycol) Biophysical Journal 68, 1921-1936.
Li, X., P. Mooney, S. Zheng, C. R. Booth, M. B. Braunfeld, S. Gubbens, D. A. Agard, Y. Cheng, 2013. Electron counting and beam-induced motion correction enable near-atomic-resolution single-particle cryo-EM. Nat Meth 10, 584-590.
Liao, M., E. Cao, D. Julius, Y. Cheng, 2013. Structure of the TRPV1 ion channel determined by electron cryo-microscopy. Nature 504, 107-112.
Parsegian, V. A., 2006. Van der Waals forces: a handbook for biologists, chemists, engineers, and physicists. Cambridge University Press, New York.
Parsegian, V. A., T. Zemb, 2011. Hydration forces: Observations, explanations, expectations, questions. Current Opinion in Colloid & Interface Science 16, 618-624.
Scheres, S. H., 2014. Beam-induced motion correction for sub-megadalton cryo-EM particles. eLife 3, e03665.

Taylor, K. A., R. M. Glaeser, 1973. Hydrophilic support films of controlled thickness and composition Review of Scientific Instruments 44, 1546-1547.

Tribet, C., R. Audebert, J. L. Popot, 1996. Amphipols: Polymers that keep membrane proteins soluble in aqueous solutions. Proceedings of the National Academy of Sciences of the United States of America 93, 15047-15050.

Vrij, A., 1966. Possible mechanism for spontaneous rupture of thin free-liquid films. Discussions of the Faraday Society, 23-33.

Wyart, F. B., J. Daillant, 1990. Drying of solids wetted by thin liquid films. Canadian Journal of Physics 68, 1084-1088.

Xu, L., A. Lio, J. Hu, D. F. Ogletree, M. Salmeron, 1998. Wetting and capillary phenomena of water on mica. Journal of Physical Chemistry B 102, 540-548.

Young, T., 1805. An Essay on the Cohesion of Fluids. Philosophical Transactions of the Royal Society of London 95, 65-87.

What is claimed is:

1. A method comprising:
   (a) providing an electron microscopy grid;
   (b) depositing an aqueous suspension including an electron microscopy sample on the electron microscopy grid;
   (c) removing a portion of the aqueous suspension from the electron microscopy grid;
   (d) after operation (c), contacting a volatile surfactant to the aqueous suspension remaining on the electron microscopy grid;
   (e) after operation (d), allowing a thickness of the aqueous suspension to decrease over a period of time; and
   (f) freezing the aqueous suspension to generate a film of the aqueous suspension having a uniform thickness disposed on the electron microscopy grid.

2. The method of claim 1, wherein a volume of aqueous suspension deposited on the electron microscopy grid is about 3 microliters or less.

3. The method of claim 1, wherein operation (c) comprises contacting an edge of the electron microscopy grid with an absorbent material.

4. The method of claim 3, wherein the absorbent material comprises filter paper.

5. The method of claim 1, wherein the electron microscopy grid includes a first surface and a second surface, and wherein operation (c) comprises contacting the first surface with an absorbent material.

6. The method of claim 1, wherein a thickness of the aqueous suspension on the electron microscopy grid is about 10 microns to 100 microns after operation (c) and before operation (d).

7. The method of claim 1, wherein operation (d) comprises contacting the volatile surfactant to the aqueous suspension using a capillary.

8. The method of claim 1, wherein operation (d) comprises exposing the aqueous suspension to vapor of the volatile surfactant.

9. The method of claim 1, wherein the volatile surfactant comprises a surfactant selected from a group consisting of chloroform and nonafluorobutyl methyl ether.

10. The method of claim 1, wherein operation (d) further comprises contacting a non-violatile surfactant to the aqueous suspension.

11. The method of claim 10, wherein the non-volatile surfactant is dissolved in the volatile surfactant.

12. The method of claim 10, wherein the non-volatile surfactant comprises a surfactant selected from a group consisting of ligands, hydrophilic polymers, phospholipid vesicles, and amphipols.

13. The method of claim 1, wherein the period of time in operation (e) is about 1 second to 300 seconds.

14. The method of claim 1, wherein operation (f) includes contacting liquid ethane to the electron microscopy grid.

15. The method of claim 1, wherein operation (f) is performed when the thickness of the aqueous suspension on the electron microscopy grid is about 100 nanometers or less.

16. The method of claim 1, wherein the electron microscopy grid includes a carbon film disposed on a first surface of the electron microscopy grid, and wherein the aqueous suspension is deposited on the carbon film.

17. The method of claim 1, wherein the electron microscopy grid has a diameter of about 3 millimeters.

18. The method of claim 1, wherein operations (b), (c), (d), and (e) are performed at a specific temperature and a specific relative humidity.

19. The method of claim 18, wherein the specific temperature is about 0° C. to 40° C., and wherein the specific relative humidity is about 50% to 100%.

20. An apparatus for preparing an electron microscopy grid, comprising:
    a chamber, the chamber defining a plurality of ports;
    a rod disposed in the chamber; and
    a sample holder attached to the rod; the apparatus operable to perform a method comprising:
    (a) receiving an electron microscopy grid in the sample holder;
    (b) receiving a deposition of an aqueous suspension including an electron microscopy sample on the electron microscopy grid;
    (c) receiving an absorbent material to remove removing a portion of the aqueous suspension from the electron microscopy grid;
    (d) after operation (c), receiving a volatile surfactant to contact contacting a volatile surfactant to the aqueous suspension remaining on the electron microscopy grid;
    (e) after operation (d), allowing a thickness of the aqueous suspension to decrease over a period of time; and
    (f) freezing the aqueous suspension to generate a film of the aqueous suspension having a uniform thickness disposed on the electron microscopy grid.

* * * * *